United States Patent [19]
Toepfer et al.

[11] Patent Number: 5,811,405
[45] Date of Patent: Sep. 22, 1998

[54] MULTIPLY FUCOSYLATED DICARBOXYLIC ACIDS POSSESSING ANTIADHESIVE PROPERTIES

[75] Inventors: Alexander Toepfer, Kriftel; Gerhard Kretzschmar, Eschborn; Eckart Bartnik, Wiesbaden-Delkenheim; Christoph Hüls, Wackarnheim; Dirk Seiffge, Mainz-Kostheim, all of Germany

[73] Assignee: Hoechst Aktiengesellschaft, Frankfurt am Main, Germany

[21] Appl. No.: 788,269

[22] Filed: Jan. 24, 1997

[30] Foreign Application Priority Data

Jan. 24, 1996 [DE] Germany .................. 196 02 355.6

[51] Int. Cl.$^6$ .................. A61K 31/70; C07H 1/00
[52] U.S. Cl. .................. 514/25; 514/23; 514/24; 514/42; 536/4.1; 536/17.2; 536/18.7; 536/124
[58] Field of Search .................. 514/23, 24, 25, 514/42; 536/4.1, 17.2, 18.7, 124

[56] References Cited

U.S. PATENT DOCUMENTS 5,654,282  8/1997  Tang et al. .................. 514/25
5,660,992  8/1997  Dasgupta et al. .................. 435/7.1

OTHER PUBLICATIONS

Huges, "Cell Adhesion Molecules—The Key to a Universal Panacea", *Scrip Magazine*, vol. 6:30–33, (Jun. 1993).

Menger et al., "Scope And Perspectives Of Intravital Microscopy—Bridge Over From in vitro to in vivo", *Immunology Today*, vol. 14(11):519–522, (1993).

Musser et al., "Structucre–Activity Studies Based On The Sialyl Lewis X Epitope", *Trends In Receptor Research*, pp. 33–40, (1993).

Brandley et al., "Structure–Function Studies On Selectin Carbohydrate Ligands. Modifications To Fucose, Sialic Acid And Sulphate As A Sialic Acid Replacement", *Glycobiology*, vol. 3(6):633–639, (1993).

Yoshida et al., "Synthesis of Chemically Modified Sialic Acid–Containing Sialyl–Le$^x$ Ganglioside Analogues Recognized by The Selectin Family", *Glycoconjugate*, vol. 10:3–15, (1993).

Harlan, "Blood", *The Journal of the American Society of Hematology*, vol. 65(3):513–525, Mar. 1985).

Springer, "Traffic Signals For Lymphocyte Recirculation and Leukocyte Emigration: The Multistep Paradigm", *Cell*, vol. 76:301–314, (1994).

Nelson et al., "Higher–Affinity Oligosaccharide Ligands For E–Selectin", *J. Clin. Invest.*, vol. 91:1157–1166, (Mar. 1993).

Buerke et al., "Sialyl Lewis—Containing Oligosaccharide Attenuates Myocardial Reperfusion Injury In Cats", *J. Clin. Invest.*, 93:1140–1148, (Mar. 1994).

Foster et al., "Production Of TNFa By LPS–Stimulated Murine, Rat And Human Blood and Its Pharmacological Modulation", *Agents Actions 38, Special Conference Issue*, pp. C77–C79, (1993).

Atherton et al., "Quantitative Investigations Of The Adhesiveness Of Circulating Polymorphonuclear Leucocytes To Blood Vessel Walls", *J. Physiol.*, vol. 222:447–474, (1972).

Aruffo et al., "CD62/P–Selectin Recognition Of Myeloid And tumor Cell Sulfatides", *Cell*, vol. 67:35–44, (Oct. 1991).

Springer, "Adhesion Receptors Of The Immune System", *Nature*, vol. 346:425–434, (Aug. 1990).

Walz et al., "Recongnition By ELAM–1 Of The Sialyl Le$^x$ Determinant On Myeloid And Tumor Cells", *Science*, vol. 250:1132–1135, (Nov. 1990).

Mulligan et al., "Protective Effects Of Oligosaccharides In P–Selectin–Dependent Lung Injury", *Nature*, vol. 364:149–151, (Jul. 1993).

Jacob et al., "Binding of Sially Lewis X To E–Selectin As Measured By Fluorescence Polarization", *Biochemistry*, vol. 34:1210–1217, (1995).

M. Israeli et al., "Co–ordination of Silver(I) to Olefinic bonds. Complex Formation between Cobalt(II), Nickel(II), Zinc(II), Cadmium(II), and Silver(I) and some Unsaturated Derivatives of Acetic and Iminodiacetic Acids," Journal of The Chemical Society, Dalton Transactions, 1975: pp. 414–417.

A. Giannis, "The Sialyl Lewis SUP x Group and its Analogues as Ligands for selectins: Chemoenzymatic Syntheses and Biological Functions," Angewandte Chemie, vol. 26, No. 2, 1994; pp. 181–191 (abstract).

F. Dasgupta et al., "Anti–Adhesive Therapeutics: A New Class of Anti–Inflammatory Agents," Exp. Opin. Invest. Drugs, Bd. 3, 1994; pp. 709–724.

*Primary Examiner*—Kathleen K. Fonda
*Attorney, Agent, or Firm*—Foley & Lardner

[57] ABSTRACT

The invention relates to multiply fucosylated dicarboxylic acid derivatives possessing antiadhesive properties, to a process for preparing them, to their use, and to pharmaceuticals and diagnostic agents which are prepared from these derivatives. These multiply fucosylated dicarboxylic acid derivatives are suitable for preparing pharmaceuticals or diagnostic agents for diseases which are associated with an excessive, selectin receptor-mediated cell adhesion in the tissue which is affected by the disease.

30 Claims, No Drawings

MULTIPLY FUCOSYLATED DICARBOXYLIC ACIDS POSSESSING ANTIADHESIVE PROPERTIES

BACKGROUND OF THE INVENTION

The invention relates to multiply fucosylated dicarboxylic acids possessing antiadhesive properties, to a process for preparing them, to their use, and to pharmaceuticals and diagnostic agents prepared from them.

At the molecular level, the circulation of blood cells such as leukocytes, neutrophils, granulocytes and monocytes is a multistep process which is very complex and only some of whose steps are known (Review: T. A. Springer, Cell 76, 301–314, 1994).

Recent research results have demonstrated that the recirculation of lymphocytes, which is crucial in immune surveillance, and the localization of neutrophils and monocytes at inflammatory foci respond to very similiar molecular mechanisms. Thus, in acute and chronic inflammatory processes, the leukocytes adhere to endothelial cells and migrate into the inflammatory focus and into the secondary lymphatic organs.

A large number of specific signal molecules, such as interleukins, leukotrienes and tumor necrosis factor (TNF), their G protein-coupled receptors and, in particular, tissue-specific cell adhesion molecules, which ensure precisely controlled recognition of the immune cells and endothelial cells, are involved in this process. Some of the most important adhesion molecules which are involved in this context, which adhesion molecules will be termed receptors in that which follows, are the electins (E, P and L selecting), the integrins and the members of the immunoglobulin superfamily.

The three selectin receptors determine the initial phase of leukocyte adhesion. E Selectin is expressed on endothelial cells for some hours after stimulation, for example by interleukin 1 (IL-1β) or tumor necrosis factor (TNF-α), while P selectin is stored in thrombocytes and endothelial cells and is presented on the cell surfaces following stimulation by thrombin, peroxide radicals or substance P, inter alia. While L selectin is expressed constantly on leukocytes, it is rapidly cleaved once again by the leukocytes during the course of the inflammation.

The adhesion of leukocytes to endothelial cells, which is mediated by selectin receptors in the initial phase of inflammatory processes, is a natural and necessary immune response to various inflammatory stimuli and to injuries to the vascular tissue. However, the course of a number of acute and chronic diseases is unfavorably influenced by excessive adhesion of leukocytes and their infiltration into the tissue concerned and also by the damage to healthy tissue in the form of an autoimmune reaction. These diseases include, for example, rheumatism, reperfusion injuries such as myocardial ischemia/infarct (MI), acute pulmonary inflammation following surgical intervention, traumatic shock and stroke, psoriasis, dermatitis, ARDS (respiratory distress syndrome in adults) and the restenosis which occurs following surgical interventions (example, angioplasty and bypass operations).

The natural ligand having the SLeX structure has already been used successfully in animal experiments in association with P selectin-dependent lung injuries (M. S. Mulligan et al., Nature 1993, 364, 149) and in association with myocardial reperfusion injuries (M. Buerke et al., J.Clin.lnvest. 1994, 93, 1140). It is reported that in initial clinical trials the compound is being employed in acute pulmonary inflammation in a dose of 1–2 grams per day and patient (communication from Cytel Corp.,/ La Jolla (Calif.) at the 2nd Glycotechnology Meeting/CHI in La Jolla/U.S.A. on 16–18 May 1994).

This high dose of active compound is in agreement with the affinity, which is known to be weak, of the natural SLex/A ligands for the selectin receptors. Thus, in all known in-vitro test systems, SLex only inhibits cell adhesion to selectin receptors at a relatively high concentration which is in the region of a $IC_{50}$ of approx. 1 mM (Jacob et al., Biochemistry 1995, 34, 1210). In the meantime, some publications and patent applications have reported efforts to obtain more strongly binding antagonists by varying the structure of the ligands. The aim of these studies is to make available antagonists which are more active and which could also potentially be employed in vivo at a lower dose.

However, variation of the fucose and neuraminic acid structural components, which have hitherto been regarded as being crucial for the structure-effect relationship (B. K. Brandley et al., Glycobiology 1993, 3, 633 and M. Yoshida et al., Glycoconjugate J. 1993, 10, 3) has not produced any significantly improved inhibition values. It was only by varying the glucosamine structural component (replacement of GlcNAc with glucose and azido groups and amino groups in position 2 of GlcNAc) that it was possible to achieve a significantly increased affinity for the E selectin receptor. On the other hand, binding to the P selectin receptor was not improved.

It is reported that the $IC_{50}$ values for these oligosaccharide derivatives for inhibiting adhesion of HL-60 and U-937 cells are in the region of 0.12 mM (as compared with 1.2–2.0 mM for SLeX) in the case of E selectin. On the other hand, a disadvantage is that binding to L and P selectins, with a value >5 mM, is markedly impaired (Dasgupta et al., Glycomed Inc. poster presentation at the La Jolla meeting in 5/94).

Generally speaking, any success for improving the binding affinity of SLex- and SLeA derivatives has up to now been restricted to the E selectin receptor, since only weak inhibitory effects, at inhibitor concentrations of approx. 1 mM, have been found in the case of the P selectin receptor (R. M. Nelson et al., J.Clin.Invest. 1993, 91, 1157).

The state of the art with regard to the binding affinity of modified SLex/A structures for selectins is reviewed in Pharmacochem. Libr. 1993, 20 (Trends in Drug Research), pp. 33–40.

SUMMARY OF THE INVENTION

It is therefore an object of the present invention to prepare novel selectin ligands which exhibit a markedly stronger binding to the receptors as compared with that of the natural ligands and are also easier to synthesize than these natural ligands.

It is a further object of the present invention to provide a pharmaceutical compound prepared from the novel selectin ligands of the present invention.

It is another object of the present invention to provide a process for administering such pharmaceutical compounds to a patient suffering from a disease associated with excessive, selectin receptor-mediated cell adhesion.

In accomplishing these and other objects there is provided a compound of the formula I

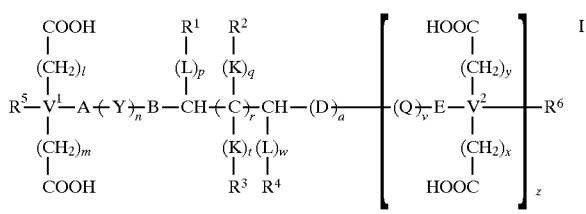

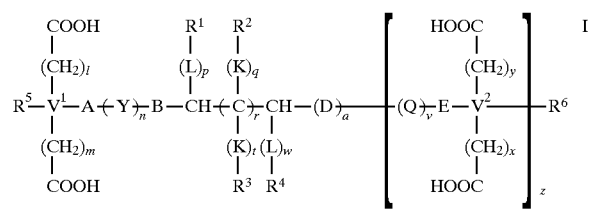

in which

R⁵ and R⁶ are, independently of each other, H, OH, COOH, NH₂, NHAc, O(CH₂)$_c$X¹, (CH₂)$_c$X¹, CH₂O(CH₂)$_c$X¹ or Z, A, B, D, E and G are, independently of each other, O, S, —NH, —HN—C(O)—, —(O)C—NH—, —O—C(O)—, —(O)C—O—, NH—C(O)—O, O—C(O)—NH, NH—C(O)—NH, S—C(O)—, (S)C—O, O—C(S)—S, S—C(S)—O, NH—C(S)—S, S—C(S)—NH, —CH₂—, —O—CH₂—, CH₂—O—, CH₂—NH— or NH—CH₂, V¹ and V² are, independently of each other, a carbon atom or a nitrogen atom, where R⁵ and R⁶ lapse in the second case, Q and Y are, independently of each other, —(CX²,X³)$_b$—, —(CX²,R⁷)$_b$—, —(CR⁷,R⁸)$_b$—, —CH₂—(CX², X³)$_b$— or a saturated or unsaturated, five-membered or six-membered carbocycle or heterocycle, or a combination of the chain —(CX²,X³)$_b$—, —(CX²,R⁷)$_b$— or —(CR⁷,R⁸)$_b$— and a carbocycle or heterocycle, where R⁷ and R⁸ are, independently of each other, H, OH, COOH, NH₂, NH—C(O)—CH₃, O(CH₂)$_d$X¹ or CH₂O(CH₂)$_d$X¹, and X¹, X² and X³ are, independently of each other, H, NH₂, COOH, OH, CH₂OH, CH₂NH₂, C₁–C₂₀-alkyl or C₆–C₁₀-aryl, K and L are, independently of each other, H—C—GZ or CH₂, R¹, R², R³ and R⁴ are, independently of each other, H, OH or G—Z, Z is a pyranoside, a pyranosyl residue which is linked via the C6 position, an alkylpyranoside which is linked via the C6 position, a furanoside, an alkylfuranoside which is linked via the C5 position, or a polyalcohol, in which one or more hydroxyl groups can, independently of each other, be substituted by R⁷ or R⁸, which is linked to G via any arbitrary position, and the indices a, b, c, d, l, m, n, p, q, t, v, w, x and y are, independently of each other, an integer from 0 to 20, and also r and z are, independently of each other, 0 or 1, where, when r is the number 0, q and t are also 0 and R² and R³ lapse.

DETAILED DESCRIPTION OF PREFERRED EMBODIMENTS

Illustrative compounds of the present invention are described as follows:

1. a compound of the formula I in which

R⁵ and R⁶ are, independently of each other, H, OH, COOH, NH₂, NHAc, —O(CH₂)$_c$X¹, (CH₂)$_c$X¹, CH₂O(CH₂)$_c$X¹ or Z, A, B, D, E and G are, independently of each other, O, S, —NH, —HN—C(O)—, —(O)C—NH—, —O—C(O)—, —(O)C—O—, NH—C(O)—O, O—C(O)—NH, NH—C(O)—NH, S—C(O)—, (S)C—O, O—C(S)—S, S—C(S)—O, NH—C(S)—S, S—C(S)—NH, —CH₂—, —O—CH₂—, CH₂—O—, CH₂—NH— or NH—CH₂, V¹ and V² are, independently of each other, a carbon atom or a nitrogen atom, where R⁵ and R⁶ lapse in the second case, Q and Y are, independently of each other, —(CX²,X³)$_b$—, —(CX²,R⁷)$_b$—, —(CR⁷,R⁸)$_b$—, —CH₂—(CX²,X³)$_b$— or a saturated or unsaturated, five-membered or six-membered carbocycle or heterocycle, or a combination of the chain —(CX²,X³)$_b$—, —(CX²,R⁷)$_b$— or —(CR⁷,R⁸)$_b$— and a carbocycle or heterocycle, where R⁷ and R⁸ are, independently of each other, H, OH, COOH, NH₂, NH—C(O)—CH₃, O(CH₂)$_d$X¹ or CH₂O(CH₂)$_d$X¹, and X¹, X² and X³ are, independently of each other, H, NH₂, COOH, OH, CH₂OH, CH₂NH₂, C₁–C₂₀-alkyl or C₆–C₁₀-aryl, K and L are, independently of each other, H—C—GZ or CH₂, R¹, R², R³ and R⁴ are, independently of each other, H, OH or G—Z, Z is a pyranoside, a pyranosyl residue which is linked via the C6 position, an alkylpyranoside which is linked via the C6 position, a furanoside, an alkylfuranoside which is linked via the C5 position, or a polyalcohol, in which one or more hydroxyl groups can, independently of each other, be substituted by R⁷ or R⁸, which is linked to G via any arbitrary position, and the indices a, b, c, d, l, m, n, p, q, t, v, w, x and y are, independently of each other, an integer from 0 to 20, and also r and z are, independently of each other, 0 or 1, where, when r is the number 0, q and t are also 0 and R² and R³ lapse, 2. preferably by a compound of the formula I wherein R⁵ is H, V¹ is C, A and Y are CH₂, B is O—CH₂, D is CH₂—O, r, p and w are the number 0, and R¹ and R⁴ are G—Z, 3. preferably wherein z is 1, Q and E are CH₂, $V^2$ is C, and $R^6$ is H, 4. particularly preferably wherein l, m, y and x are the number 0, G is O, and Z is a pyranoside, 5. where the pyranoside Z is preferably an L-fucoside, for example

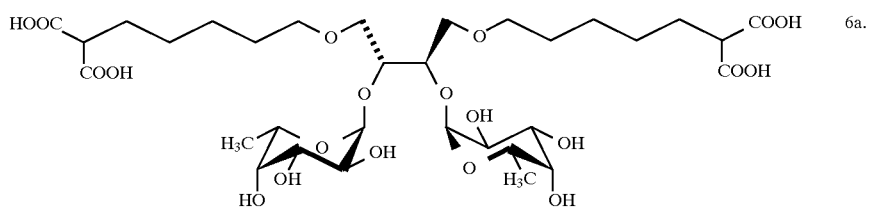

6a.

6. Preferably, the compound of the formula I has the features given under No. 2 and also the following features:

z is the number 0, and $R^6$ is Z, 7. preferably wherein l and m are the number 0, G is O, and Z is a pyranoside, 8. where the pyranoside Z is particularly preferably an L-fucoside, for example

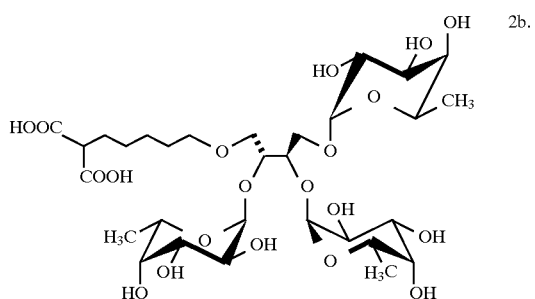

2b.

9. A further preferred embodiment of the present invention is a compound of the formula I wherein $R^1$, $R^4$ and $R^5$ are H, $V^1$ is C, A and Y are $CH_2$, B and D are O, p and w are the number 0, r is 1, K is $CH_2$, and $R^2$ and $R^3$ are GZ, 10. preferably wherein z is 1, Q and E are $CH_2$, $V^2$ is C, and $R^6$ is H, 11. particularly preferably wherein l, m, x and y are the number 0, q and t are 1, G is O, and Z is a pyranoside, where the pyranoside Z is preferably an L-fucoside, for example

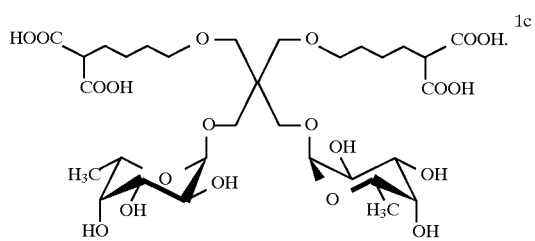

1c

13. A further embodiment of the present invention is a compound of the formula I wherein $R^5$ is H, $V^1$ is C, A and Y are $CH_2$, B and D are O, and r is the number 0, 14. preferably wherein z is 1, $R^6$ is H, Q and E are $CH_2$, and $V^2$ is C, 15. particularly preferably wherein l, m, y and x are the number 0, p and w are 2, L is H—C—GZ, $R^1$ and $R^4$ are H, G is O, and Z is a pyranoside, where 16. the pyranoside Z is particularly preferably an L-fucoside, for example

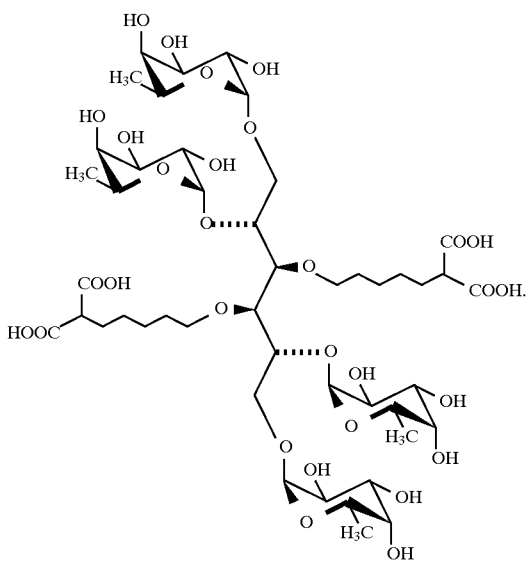

17. A further embodiment of the present invention is a compound of the formula I wherein a, p, r, w and z are the number 0, $R^5$ and $R^6$ are H, $V^1$ is C, A and Y are $CH_2$, B is $O-CH_2$, and $R^1$ and $R^4$ are G—Z, 18. preferably wherein l and m are the number 0, G is O, and Z is a pyranoside, where 19. the pyranoside is preferably an L-fucoside, for example

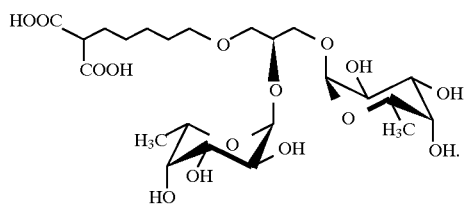

20. The object which was initially set is furthermore achieved by a process for preparing a compound of the formula 1, wherein, by alkylating, acylating or glycosylating a functional group $L^1$ or two functional groups $L^1$ and $L^2$, simultaneously or in succession, of an acceptor of the formula II

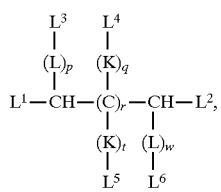

in which the remaining functional groups, and also the functional groups $L^n$ (n 2–6 or 3–6, respectively), are protected if necessary, with a donor III

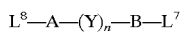

which is provided with an activated functional group $L^7$, and, if $L^2$ is also unprotected, with a donor IV

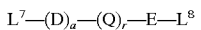

which is provided with an activated functional group $L^7$, whose remaining functional groups, and the functional group $L^8$, carry protecting groups if necessary, intermediate compound V

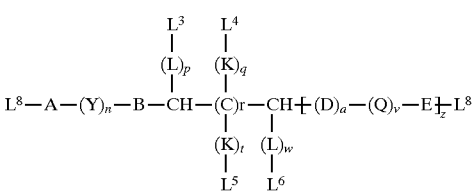

is initially prepared, where the donors III and IV can be different or identical, after which the functional groups of the intermediate compound V on the atom groups K and L and, where appropriate, the protecting groups of the functional groups $L^3$ to $L^6$ and $L^8$ are selectively removed and the selectively deprotected intermediate compound V is reacted with one or more glycosyl or polyol donors VI

where $L^9$ is an activated functional group and the remaining functional groups of the donor VI are protected if necessary, and, after selective deprotection of the functional groups $L^8$, alkylated with the alkyl donor VII

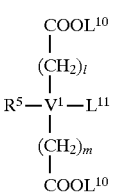

alkyl donor VIII

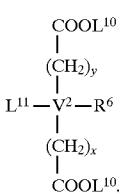

where $L^{10}$ is a carboxyl protecting group and $L^{11}$, where appropriate in combination with $V^1$ or $V^2$, is an alkylating group, and is finally converted, by removing all the protecting groups, into a compound of the formula I as claimed in one of claims 1 to 16, with all the remaining variables having the meanings mentioned under No. 1.

21. If desired, the acceptor II can also first of all be reacted with one or more glycosyl donors or polyol donors VI, and then reacted with donor IV in order to form the intermediate compound V.

a) The compounds described under Nos. 5 and 8 may preferably be prepared, using the process according to the invention, by using (−)-2,3-O-isopropylidene-L-threitol as acceptor II, 5-allyloxy-1-p-toluenesulfonyloxypentane as donors III and IV, and O-(2,3,4-tri-O-benzyl-α/β-L-fucopyranosyl) trichloroacetimidate as glycosyl donor VI. After the two allyl groups have been eliminated, and the resulting hydroxyl groups have been tosylated or brominated, alkylation is effected using dimethyl malonate, as alkyl donor VII, after which deprotection takes place.

b) The compound described under No. 11 may preferably be prepared, using the process according to the invention, by using isopropylidene-pentaerythritol as acceptor II and subsequently reacting as described under a).

c) The compound described under No. 16 may preferably be prepared, using the process according to the invention, by using 1,2:5,6-di-O-isopropylidene-D-mannitol as acceptor II and subsequently reacting as described under a).

d) The compound described under No. 19 may advantageously be prepared, using the process according to the invention, by using D-α/β-isopropylidene-glycerol as acceptor II and subsequently reacting with the alkyl donor VII as described under a).

Despite having a lower molar mass than sialyl Lewis X, the compounds of the formula I according to the invention can have a higher affinity for the natural receptors, for example for E selectin and P selectin, than does sialyl Lewis X. This can be demonstrated using the cell adhesion assays which are described below.

Primary assays for investigating the effect of the compounds according to the present invention on the adherence of cells to recombinant, soluble selectin fusion proteins.

In order to test the efficacy of the compounds according to the invention of the interaction between the E and P selectins (old nomenclature, ELAM-1 and GMP-140, respectively) and their ligands, an assay is used which is in each case specific for only one of these interactions. The ligands are presented in their natural form as surface structures on promyelocytic HL60 cells. Since HL60 cells exhibit ligands and adhesion molecules of a very wide variety of specificities, the desired specificity of the assay can only be generated by way of the binding partner. Recombinantly prepared soluble fusion proteins, formed from the extracytoplasmic domain of either E selectin or P selectin and the constant region of a human immunoglobulin of the IgG1 subclass, were used as binding partners.

Preparation of L selektin-IgG1

The gene construct "ELAM-Rg", published by Walz et al., 1990, was used to prepare soluble L-selectin-IgG1 fusion protein.

For the purposes of expression, the plasmid DNA was transfected into COS-7 cells (ATCC) using DEAE dextran (molecular biological methods: see Ausubel, F. M., Brent, R., Kingston, R. E., Moore, D. D., Seidman, J. G., Struhl, K. and Smith, J. A. 1990. Current Protocols in Molecular Biology, John Wiley, New York). Seven days after the transfection, the culture supernatant is isolated, freed from cells and cell fragments by centrifugation, brought to 25 mM Hepes, pH 7.0, 0.3 mM PMSF, 0.02% sodium azide, and stored at +4° C. (Walz, G., Aruffo, A., Kolanus, W., Bevilacqua, M. and Seed, B. 1990. Recognition by ELAM-1 of the sialyl-Lex determinant on myeloid and tumor cells. Science 250, 1132–1135.)

Preparation of P selectin-IgG1

The gene construct "CD62Rg", published by Aruffo et al., 1991, is used to prepare the soluble P selectin-IgG1 fusion protein. The subsequent procedure corresponds to the preparation of L selectin-IgG1 which was described in A1. Aruffo, A., Kolanus, W., Walz, G., Fredman, P. and Seed, B. 1991. CD62/-P-Selectin recognition of myeloid and tumor cell sulfatides. Cell 67, 35–44.

Preparation of CD4-IgG1

The gene construct "CD4:IgG1 hinge", published by Zettelmeissl et al., 1990, is used to prepare the soluble CD4-IgG1 fusion protein. The subsequent procedure corresponds to the preparation of L selectin-IgG1 which was described in A1. (Zettelmeissl, G., Gregersen, J.-P., Duport, J. M., Mehdi, S., Reiner, G. and Seed, B. 1990. Expression and characterization of human CD4: Immunoglobulin Fusion Proteins. DNA and Cell Biology 9, 347–353.)

Implementation of the HL60 cell adhesion assay on recombinant, soluble adhesion molecules 1. 96-well microtiter test plates (Nunc Maxisorb) are incubated, at room temperature for 2 hrs, with 100 µl of a goat anti-human IgG antibody (Sigma) which has been diluted (1+100) in 50 mM Tris, pH 9.5. After the antibody solution has been removed, the plates are washed once with PBS.

2. 150 µl of the blocking buffer are left in the wells for 1 hr. at room temperature. The composition of the blocking buffer is: 0.1% gelatin, 1% BSA, 5% calf serum, 0.2 mM PMSF, 0.02% sodium azide. After the blocking buffer has been removed, the plates are washed once with PBS.

3. In each case, 100 µl of cell culture supernatant from appropriately transfected and expressing COS cells are pipetted into the wells. The plates are then incubated at room temperature for 2 hrs. After the cell culture supernatant has been removed, the plates are washed once with PBS.

4. 20 µl of binding buffer are added to the wells. The binding buffer has the composition: 50 mM Hepes, pH 7.5; 100 mM NaCl; 1 mg/ml BSA; 2 mM $MgCl_2$; 1 mM $CaCl_2$; 3 mM $MnCl_2$; 0.02% sodium azide: 0.2 mM PMSF. 5 µl of the test substance are then added to this by pipetting, after which the plate is mixed by swivelling and incubated at room temperature for 10 min.

5. 50 ml of a culture of HL60 cells, containing 200,000 cells/ml, are centrifuged at 350 g for 4 min. The pellet is resuspended in 10 ml of RPMI 1640 and the cells are centrifuged once again. In order to label the cells, 50 µg of BCECF-AM (Molecular Probes) are dissolved in 5 µl of anhydrous DMSO; 1.5 ml of RPMI 1640 are then added to the BCECF-AM/DMSO solution. The cells are resuspended in this solution, and the suspension is incubated at 37° C. for 30 min. Following a two-minute centrifugation at 350 g, the labeled cell pellet is resuspended in 11 ml of binding buffer and the resuspended cells are distributed between the microtiter plate wells in 100 µl aliquots. The plate is left to stand at room temperature for 10 min in order to allow the cells to sediment to the bottom of the test plate. This gives the cells the opportunity of adhering to the coated plastic.

6. In order to stop the test, the microtiter plate is completely immersed, at an angle of 45°, in the stopping buffer (25 mM Tris, pH 7.5; 125 mM NaCl; 0.1% BSA; 2 mM $MgCl_2$; 1 mM $CaCl_2$; 3 mM $MnCl_2$; 0.02% sodium azide). The stopping buffer is removed from the wells by inversion and the procedure is repeated a further two times.

7. The quantity of BCECF-AM-labeled cells adhering in the wells is measured in a cytofluorimeter (Millipore) at a sensitivity setting of 4, an excitation wavelength of 485/22 nm and an emission wavelength of 530/25 nm.

Results:

Compound 6a:

$IC_{50}$ (E-selectin)=0.5–1.5 mM $IC_{50}$ (P-selectin)=3.5–4.1 mM

Leukocyte adhesion—Examination of the efficacy of the compounds according to the invention in vivo (intravital microscopy on the rat):

Tissue destruction caused by leukocytes which are immigrating or blocking the microcirculation plays a crucial role in inflammatory processes and other conditions which activate the cytokines. The first phase, and that which is crucial for the subsequent disease process, is the activation of leukocytes within the circulation, in particular in the precapillary and postcapillary regions. During this phase, the leukocytes adhere, first of all, after they have left the axial blood circulation, to the inner vascular wall, i.e. to the vascular endothelium. All the subsequent leukocyte effects, i.e. the active migration through the vascular wall and the subsequent, oriented migration in the tissue, are consequential reactions (Harlan, J. M., Leukocyte-endothelial interaction, Blood 65, 513–525, 1985).

This receptor-mediated interaction of leukocytes and endothelial cells is regarded as an initial sign of the inflammatory process. In addition to the adhesion molecules which have already been expressed physiologically, there is a chronologically graduated, massive expression, under the influence of inflammatory mediators (leukotrienes and PAF) and cytokines (TNF-alpha and interleukins), of adhesion molecules on the cells. At present, these molecules are subdivided into three groups: 1. immunoglobulin gene superfamily, 2. integrins and 3. selectins. While the adhesion between molecules of the lg gene superfamily and the protein-protein bonds is taking place, lectin-carbohydrate bonds are prominent in the cooperation between selectins (Springer, T. A., Adhesion receptors of the immune system. Nature 346, 425–434, 1990; Huges, G., Cell adhesion molecules—the key to a universal panacea, Scrips Magazine 6, 30–33, 1993; Springer, T. A., Traffic signals for lymphocyte recirculation and leukocyte emigration; The multistep paradigm. Cell 76, 301–314, 1994).

Method:

The induced adhesion of leukocytes is quantified in the rat mesentery using an intravital microscopic investigation technique (Atherton A. and Born G. V. R., Quantitative investigations of the adhesiveness of circulating polymorphonuclear leukocytes to blood vessel walls. J. Physiol. 222, 447–474, 1972); herein incorporated by reference. A prolonged anesthesia is instituted, under inhalation anesthesia with ether, by injecting urethane (1.25 mg/kg of body weight) intramuscularly. Blood vessels (femoral vein for injection of substances and carotid artery for measuring blood pressure) are exposed by dissection and catheters are then tied into them. After that, the corresponding transparent tissue (mesentery) is exposed spread out on a microscope stage and overlaid with paraffin oil at 37° C. (Menger, M. D. and Lehr, H., A. Scope and perspectives of intravital microscopy-bridge over from in vitro to in vivo, Immunology Today 14, 519–522, 1993); herein incorporated by reference. The test substance is administered i.v. to the animal (10 mg/kg). The experimental increase in blood cell adhesion is triggered, by means of cytokine activation, by systemically administering lipopolysaccharide (LPS, 15 mg/kg) 15 minutes after having administered the test substance (Foster S. J., McCormick L. M., Ntolosi B. A. and Campbell D., Production of TNF-alpha by LPS-stimulated murine, rat and human blood and its pharmacological modulation, Agents and Actions 38, C77–C79, 1993, 18.01.1995); herein incorporated by reference. The resulting increase in the adhesion of leukocytes to the endothelium is quantified directly by means of vital microscopy or using fluorescence dyes. All measurement procedures are filmed with a video camera and stored on a video recorder. The number of rolling leukocytes (i.e. all leukocytes which are visibly rolling and which are slower than the flowing erythrocytes) and the number of leukocytes which are adhering to the endothelium (dwell time longer than 5 seconds) are recorded every 10 minutes for a period of 60 minutes. After the experiment has finished, the anesthetized animals are put down painlessly and without excitation by systemically injecting T61. For the purposes of evaluation, the results from each of 8 treated animals are compared with those from each of 8 untreated animals (control group) (the results are given as percentage values).

Results:

Compound 6a:

Dose: 10 mg/kg; administration: i.v.; species: SPRD(m); weight: 298±17.72 g; number of vessels: 14; vessel diameter: 26±2 $\mu$m; leukocytes: $(6.0\pm1.09)\cdot10^3/mm^3$; fibrinogen 130±6.95 mg/100 ml; inhibition: 39%.

Reperfusion model for investigating the influence of neutrophil adhesion in the course of ischemialreperfusion carried out on the open rabbit heart.

The hearts are perfused with nutrient solution, and also with/without leukocytes and/or active compound, at constant pressure using the Langendorff technique. After that, an ischemia is elicited by ligating the left coronary artery (30 min). Following reperfusion (30 min), the accumulation of leukocytes is evaluated histologically. During the course of the experiment, potentials and arrhythmias are measured at 256 electrodes (total duration of the experiment, approx. 90 min). While pronounced arrhythmias occur in 6 out of 7 untreated hearts which are perfused with leukocytes, due to the leukocyte infiltration, less leukocyte accumulation and fewer arrhythmias are seen in hearts which are treated with an active compound (RGDS peptides or chondroitin sulfate). The compounds according to the present invention, and also their physiologically tolerated salts, are very well suited, owing to their valuable pharmacological properties, for use as medicines in mammals, in particular humans.

The present invention therefore also relates to a pharmaceutical which comprises at least one compound of the formula I, or its pharmacologically tolerated salts, and to its use for preparing a pharmaceutical for the therapy or prophylaxis of diseases which are associated with an excessive, selectin receptor-mediated cell adhesion in the tissue which is affected by the disease, for example autoimmune diseases, such as rheumatism, or cardiovascular diseases, such as reperfusion damage, ischemia or cardiac infarct.

Salts with inorganic and organic bases, for example NaOH, KOH, $Mg(OH)_2$, $Ca(OH)_2$, diethanolamine or ethylenediamine, or with amino acids, such as arginine, lysine or glutamic acid, are particularly suitable for use as pharmacologically tolerated salts of the compound of the formula I. They are prepared in accordance with standard protocols.

The pharmaceuticals are particularly suitable for treating acute and chronic inflammations which can be characterized pathophysiologically by a disturbance of the cell circulation, for example of lymphocytes, monocytes and neutrophil granulocytes. These inflammations include autoimmune diseases, such as acute polyarthritis, rheumatoid arthritis and insulin-dependent diabetes (diabetes mellitus, IDDM), acute and chronic transplant rejections, shock lung (ARDS, adult respiratory distress syndrome), inflammatory and allergic skin diseases, such as psoriasis and contact eczema, cardiovascular diseases, such as myocardial infarct, reperfusion damage following thrombolysis, angioplasty or bypass operations, septic shock and systemic shock. A further potential indication is the treatment of metastasizing tumors, since tumor cells carry surface antigens which possess both sialyl Lewis X and sialyl Lewis A structures as recognition epitopes. Over and above this, these pharmaceuticals, which are stable in the acid medium of the stomach, can be employed for the antiadhesive therapy of *Helicobacter pylori* and related microorganisms, where appropriate also in combination with antibiotics. In addition, it is possible to conceive of developing a therapy for the cerebral form of malaria using these pharmaceuticals.

While the pharmaceuticals according to the invention are generally administered intravenously, orally or parenterally, or as implants, they can, in principle, also be used rectally. Examples of suitable solid or liquid pharmaceutical preparation forms are granules, powders, tablets, coated tablets, (micro-)capsules, suppositories, syrups, emulsions, suspensions, aerosols, drops or injectable solutions in ampoule form, and also preparations having a protracted release of active compound, in the preparation of which excipients and additives, and/or adjuvants, such as disintegrants, binders, coating agents, swelling agents, glidants, lubricants, flavorants, sweeteners or solubilizers, are customarily used. Examples of frequently used excipients or adjuvants which may be mentioned are magnesium carbonate, titanium dioxide, lactose, mannitol and other sugars, talc, lactalbumin, gelatin, starch, vitamins, cellulose and its derivatives, animal and vegetable oils, polyethylene glycols and solvents, such as sterile water, alcohols, glycerol and polyhydric alcohols.

The pharmaceutical preparations are preferably prepared and administered in dosage units. Tablets, capsules and suppositories are solid dosage units. Different daily doses are necessary for treating a patient, depending on the activity of the compound, the type of administration, the nature and severity of the disease, and the age and body weight of the patient. However, both higher or lower daily doses may possibly be appropriate. The daily dose may be administered both by means of a single administration in the form of a single dose unit, or else several small dosage units, and by the repeated administration of subdivided doses at defined intervals. The daily dose which is to be administered may also depend on the number of receptors which are expressed during the course of the disease. It is conceivable that only a few receptors are expressed on the cell surface in the initial stage of the disease and, as a consequence, the daily dose which is to be administered is lower than in the case of severely diseased patients.

The pharmaceuticals according to the invention are prepared by using customary excipients and, where appropriate, additives and/or adjuvants to bring a compound according to the present invention into the, or a, suitable form for administration.

Examples of the preparation of the compounds according to the invention:

Example 1 a) Synthesis of 1,4-bis(5-allyloxy-1-pentyloxy)-D-threitol (COMPOUND 1a) and 1-(5-allyloxy-1-pentyloxy)-D-threitol (COMPOUND 1b):

A mixture of 2,3-O-isopropylidene-D-threitol (1.38 g, 8.51 mmol) and sodium hydride (572 mg, 23.83 mg) in dimethylformamide (100 ml) is stirred at room temperature for 30 min. 5-Allyloxy-1-pentyloxytoluenesulfonate (6.6 g, 22.19 mmol) is then added dropwise at 0° C. The mixture is subsequently left to stir at room temperature for 2 days. Water (20 ml) and diethyl ether (400 ml) are added for the working-up. The organic phase is washed with water (3×140 ml), dried over sodium sulfate, filtered and concentrated. The residue is treated with 50% trifluoroacetic acid (250 ml) at 60° C. for 45 min. After concentrating, the residue is purified chromatographically, toluene/acetone 5:1→4:1→3:1→2:1→1:1. 1a (2.1 g, 67%) and 1b (284 mg, 13%) are obtained.

The yield of 1b can be increased to more than 60% by using only 0.8 equivalents, instead of 2.8 equivalents, of 5-allyloxy-1-pentyloxytoluenesulfonate. 1a: $^1$H-NMR (300 MHz, CDCl$_3$): δ=1.42 (m, 4H, 2 CH$_2$),1.60 (m, 8 H, 4 CH$_2$), 2.86 (bd, 2H, 2 OH), 3.42 (m, 12H, 6 CH$_2$), 3.82 (m, 2H, 2-H$_{threit}$, 3-H$_{threit}$), 3.96 (m, 4H, 2 CH2—CH=CH2), 5.22 (m, 4H, 2 CH2—CH=CH2), 5.92 (m, 2H, 2 CH2—CH=CH2). 1b: $^1$H-NMR (300 MHz, CDCl$_3$): δ=1.42 (m, 2H, CH$_2$), 1.60 (m, 4 H, 2 CH$_2$), 3.42–3.84 (m, 13H, 4 CH$_2$, 2-H$_{threit}$, 3-H$_{threit}$, 3 OH), 3.96 (m, 2H, CH2—CH=CH2), 5.22 (m, 2H, CH2—CH=CH2), 5.92 (m, 1 H, CH2—CH=CH2).

b) Synthesis of 1,4-bis(5-allyloxy-1-pentyloxy)-2,3-bis(2,3,4-tri-O-benzyl-α-L-fucopyranosyl)-D-threitol (COMPOUND 2a):

A 0.1M solution of trimethylsilyl trifluoromethanesulfonate (0.9 ml) is added to a solution of 1a (1.15 g, 3.09 mmol) in diethyl ether (30 ml). Immediately thereafter, a solution of O-(2,3,4-tri-O-benzyl-α/β-L-fucopyranosyl)-trichloroacetimidate (5.0 g, 8.6 mmol) in diethyl ether (10 ml) is added dropwise within the space of 5 min. After 30 min, sodium hydrogen carbonate (0.25 g) is added and the mixture is filtered and concentrated; the residue is then chromatographed (hexane/ethyl acetate 4:1 3:1). 2a (3.21 g, 86%) is obtained.

$^1$H-NMR (300 MHz, CDCl$_3$): δ=1.10 (d, 3 H, CH$_{3fuc}$), 5.18 (m, 4H, 2 CH2—CH=CH2), 5.88 (m, 2H, 2 CH2—CH=CH2).

c) Synthesis of 1,4-bis(5-hydroxy-1-pentyloxy)-2,3-bis(2,3,4-tri-O-benzyl-α-L-fucopyranosyl)-D-threitol (COMPOUND 3a):

A mixture of 2a (3.21 g, 2.66 mmol) and rhodium tris(triphenylphosphine) chloride (0.247 mmol, 0.267 mmol) in ethanol/water (9:1, 100 ml) is boiled under reflux for 2 h. After concentrating, the residue is purified by means of chromatography (toluenelacetone/methanol 5:1:0.1). 3a (1.53 g, 51%) is obtained.

d) Synthesis of 1,4-bis(5-bromo-1-pentyloxy)-2,3-bis(2,3,4-tri-O-benzyl-α-L-fucopyranosyl)-D-threitol (COMPOUND 4a):

Triethylamine (3.8 ml, 27.44 mmol) and 1,2-dibromotetrachloroethane (4.47 g, 13.72 mmol) are added, at 0° C., to a solution of 3a (7.7 g, 6.86 mmol) and triphenylphosphine (3.6 g, 13.72 mmol) in dichloromethane (250 ml). After 90 min, the mixture is concentrated and the residue is purified chromatographically, hexanelethyl acetate (3:1). Yield of 4a: 5.8 g (68%).

e) Synthesis of 1,4-bis(5-malonyl-1-pentyloxy)-2,3-bis(2,3,4-tri-O-benzyl-α-L-fucopyranosyl)-D-threitol (COMPOUND 5a):

A mixture of 4a (5.8 g, 4.64 mmol), dimethyl malonate (243 ml), potassium carbonate (12.49 g) and dibenzo-18-crown-6 (3.35 g) is stirred at 100° C. for 3 h. For the working-up, the mixture is diluted, after having been cooled, with dichloromethane (2.5 l) and filtered with suction through kieselguhr; the organic phase is then treated alternately with water (110 ml) and dry ice until the pH of the aqueous phase is neutral. Drying takes place over sodium sulfate, followed by filtration and concentration, and the residue is chromatographed (hexane/ethyl acetate 4:1→3:1→2:1). 5a (5.6 g, 94%) is obtained.

$^1$H-NMR (300 MHz, CDCl$_3$): δ=1.10 (δ, 6H, 2 CH$_{3fuc}$), 1.26 (m, 12H, 6 CH$_2$),1.47 (m, 4H),1.83 (m, 4H), 3.70 (2s, 12H, 4 COOCH$_3$), 5.29 (d, 2H, 2 1-H$_{fuc}$).

f) Synthesis of 1,4-bis(5-malonyl-1-pentyloxy)-2,3-bis(α-L-fucopyranosyl)-D-threitol (COMPOUND 6a):

A mixture of 5a (2.8 g, 2.19 mmol) and palladium carbon (10%, 2.8 g) in methanol/dioxane (10:1, 330 ml) is hydrogenated in a hydrogen atmosphere for 24 h under standard pressure. The palladium carbon is filtered off and the remaining mixture is concentrated and treated with 1M sodium hydroxide solution (100 ml). After 2 h, the mixture is neutralized with Amberlite IR-120 and purified through RP silica gel ($C_{18}$ Bakerbond 60 Å) using water/methanol 9:1→1:9. 6a (1.11 g, 67%) is obtained.

$^1$H-NMR (300 MHz, $D_2O$): δ=1.17 (d, 6H, 2 $CH_{3fuc}$), 1.26 (m, 4H, 2 $CH_2$), 1.52 (m, 4H, 2 $CH_2$), 1.66 (m, 4H, 2 $CH_2$) 4.20 (q, 2H, 2 5-$H_{fuc}$), 5.07 (d, 2H, 2 1-$H_{fuc}$).

Example 2 a) Synthesis of 1-(5-malonyl-1-pentyloxy)-2,3,4-tris(α-L-fucopyranosyl)-D-threitol (COMPOUND 2b):

Compound 2b is synthesized in an analogous manner to 6a, but with the difference that 1b is used instead of 1a.

$^1$H-NMR (300 MHz, $D_2O$): δ=1.18 (3 d, 9H, 3 $CH_{3fuc}$), 1.26 (m, 2H, $CH_2$), 1.53 (m, 2H, $CH_2$), 1.67 (m, 2H, $CH_2$), 4.84, 5.06, 5.16 (3 d, 3H, 3 1-$H_{fuc}$).

Example 3 a) Synthesis of bis(4-malonyl-1-butyloxy)-bis(α/β-L-fucopyranosyl)-pentaerythritol (COMPOUND 1c):

Compound 1c is synthesized in an analogous manner to 6a, but with the difference that O-isopropylidene-pentaerythritol is used instead of 2,3-O-isopropylidene-D-threitol.

$^1$H-NMR (300 MHz, $D_2O$): δ=1.10, 1.12 (2 d, 6H, 2 $CH_{3fuc}$), 4.17, 4.19, 4.70 (3 d, 2H, 2 1-$H_{fuc}$).

Example 4 a) Synthesis of 1,2-bis(α-L-fucopyranosyl)-3-(5-malonyl-1-pentyloxy)- D-glycerol (COMPOUND 1d):

Compound 1d is synthesized in an analogous manner to 6a, but with the difference that D-α/β-isopropylidene-glycerol is used instead of 2,3-O-isopropylidene-D-threitol.

$^1$H-NMR (300 MHz, $D_2O$): δ=1.10, (2d, 6H, 2 $CH_{3fuc}$), 4.75, 4.96 (2 d, 2H, 2 1-$H_{fuc}$).

Example 5 a) Synthesis of 1,2,5,6-tetrakis(α-L-fucopyranosyl)-3,4-bis(5-malonyl-1-pentyloxy)-D-mannitol (COMPOUND 1e):

Compound 1e is synthesized in an analogous manner to 6a, but with the difference that 1,2:5,6-di-O-isopropylidene-D-mannitol is used instead of 2,3-O-isopropylidene-D-threitol.

$^1$H-NMR (300 MHz, $D_2O$): δ=1.10, (d, 12H, 4 $CH_{3fuc}$), 4.26, 4.79, 5.07 (3 d, 2H, 2 1 -$H_{fuc}$).

The preferred embodiments set forth above are to illustrate the invention and are not intended to limit the methods and products of the present invention. Additional embodiments and advantages within the scope of the claimed invention will be apparent to one of ordinary skill in the art.

German priority application 19602355.6, filed Jan. 24, 1996, including the specification, any drawings, claims and abstract, is hereby incorporated by reference.

We claim:

1. A compound of the formula I

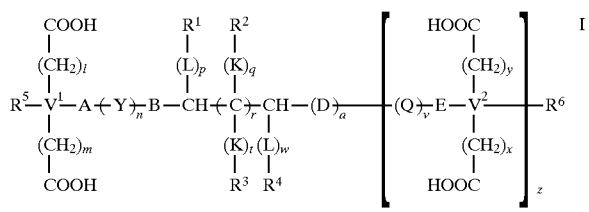

in which

R$^5$ and R$^6$ are, independently of each other, H, OH, COOH, $NH_2$, NHAc, $O(CH_2)_cX^1$, $(CH_2)_cX^1$, $CH_2O(CH_2)_cX^1$ or Z, A, B, D, E are, independently of each other, O, S, —NH, HN—C(O)—, —(O)C—NH—, —O—C(O)—, —(O)C—O—, NH—C(O)—O, O—C(O)—NH, NH—C(O)—NH, S—C(O)—, (S)C—O, O—C(S)—S, S—C(S)—O, NH—C(S)—S, S—C(S)—NH, —$CH_2$—, —O—$CH_2$—, $CH_2$—O—, $CH_2$—NH— or NH—$CH_2$, V$^1$ and V$^2$ are, independently of each other, a carbon atom or a nitrogen atom, where R$^5$ and R$^6$ lapse when V$^1$ or V$^2$ is a nitrogen atom, Q and Y are, independently of each other, —(CX$^2$ or X$^3$)$_b$—, —(CX$^2$ or R$^7$)$_b$—, —(CR$^7$ or R$^8$)$_b$—, —$CH_2$—(CX$^2$ or X$^3$)$_b$— or a saturated or unsaturated, five-membered or six-membered carbocycle or heterocycle, or a combination of the chain —(CX$^2$ or X$^3$)$_b$—, —(CX$^2$ or R$^7$)$_b$— or —(CR$^7$ or R$^8$)$_b$— and a carbocycle or heterocycle, where R$^7$ and R$^8$ are, independently of each other, H, OH, COOH, $NH_2$, NH—C(O)—$CH_3$, $O(CH_2)_dX^1$ or $CH_2O(CH_2)_dX^1$, and X$^1$, X$^2$ and X$^3$ are, independently of each other, H, $NH_2$, COOH, OH, $CH_2OH$, $CH_2NH_2$, $C_1$–$C_{20}$-alkyl or $C_6$–$C_{10}$-aryl, K and L are, independently of each other, H—C—GZ or $CH_2$, R$^1$, R$^2$, R$^3$ and R$^4$ are, independently of each other, H, OH or G—Z, Z is a fucopyranoside, a fucopyranosyl residue which is linked via the C6 position, an alkylfucopyranoside which is linked via the C6 position, a fucofuranoside, or an alkylfucofuranoside which is linked via the C5 position, in which one or more hydroxyl groups can, independently of each other, be substituted by R$^7$ or R$^8$, wherein said G—Z link is such that Z is linked to G via a carbon atom, the indices a, b, c, d, l, m, n, p, q, t, v, w, x and y are, independently of each other, an integer from 0 to 20, and also r and z are, independently of each other, 0 or 1, where, when r is the number 0, q and t are also 0 and R$^2$ and R$^3$ lapse, G is O, S, —NH, —HN—C(O)—, —(O)C—NH—, —O—C(O)—, —(O)C—O—, NH—C(O)—O, O—C(O)—NH, NH—C(O)—NH, S—C(O)—, (S)C—O, O—C(S)—S, S—C(S)—O, NH—C(S)—S, S—C(S)—NH, —$CH_2$—, —O—$CH_2$—, $CH_2$—O—, $CH_2$—NH— or NH—$CH_2$, and wherein said formula I contains two or more Z molecules.

2. The compound as claimed in claim 1, wherein a is 1,

R$^5$ is H, $V^1$ is C,
A and Y are $CH_2$,
B is O—$CH_2$,
D is $CH_2$—O,
r, p and w are the number 0, and
$R^1$ and $R^4$ are G—Z.
3. The compound as claimed in claim 1, wherein
z is 1,
Q and E are $CH_2$,
$V^2$ is C, and
$R^6$ is H.
4. The compound as claimed in claim 1, wherein
l, m, y and x are the number 0,
G is O, and
Z is a fucoside.
5. The compound as claimed in claim 1, wherein Z is an L-fucoside.
6. The compound as claimed in claim 1, wherein
z is the number 0, and
$R^6$ is Z.
7. The compound as claimed in claim 1, wherein
l and m are the number 0,
G is O, and
Z is a fucoside.
8. The compound as claimed in claim 7, wherein Z is an L-fucoside.
9. The compound as claimed in claim 1, wherein
a is 1,
$R^1$, $R^4$ and $R^5$ are H,
$V^1$ is C,
A and Y are $CH_2$,
B and D are O,
p and w are the number 0,
r is 1,
K is $CH_2$, and
$R^2$ and $R^3$ are GZ.
10. The compound as claimed in claim 1, wherein
z is 1,
Q and E are $CH_2$,
$V^2$ is C, and
$R^6$ is H.
11. The compound as claimed in claim 1, wherein
l, m, x and y are the number 0,
q and t are 1,
G is O, and
Z is a fucoside.
12. The compound as claimed in claim 1, wherein Z is an L-fucoside.
13. The compound as claimed in claim 1, wherein
a is 1,
$R^5$ is H,
$V^1$ is C,
A and Y are $CH_2$,
B and D are O, and
r is the number 0.
14. The compound as claimed in claim 1, wherein
z is 1,
$R^6$ is H,
Q and E are $CH_2$, and
$V^2$ is C.
15. The compound as claimed in claim 1, wherein
l, m, y and x are the number 0,
p and w are 2,
L is H—C—GZ,
$R^1$ and $R^4$ are H,
G is O, and
Z is a pyranoside.
16. The compound as claimed in claim 13, wherein Z is an L-fucoside.
17. The compound as claimed in claim 1, wherein
a,p,r,w and z are the number 0,
$R^5$ and $R^6$ are H,
V1 is C,
A and Y are $CH_2$,
B is O—$CH_2$, and
$R^1$ and $R^4$ are G—Z.
18. The compound as claimed in claim 1, wherein
l and m are the number 0,
G is O, and
Z is a fucoside.
19. The compound of claim 1, wherein Z is an L-fucoside.
20. A process for preparing a compound of the formula I as claimed in claim 1, wherein, by alkylating, acylating or glycosylating a functional group $L^1$ or two functional groups $L^1$ and $L^2$, simultaneously or in succession, of an acceptor of the formula II $$L^1-CH-\underset{\underset{L^5}{|}}{\overset{\overset{L^3}{|}}{\underset{(K)_t}{\overset{(L)_p}{|}}}}-(C)_r-\underset{\underset{L^6}{|}}{\overset{\overset{L^4}{|}}{\underset{(L)_w}{\overset{(K)_q}{|}}}}-CH-L^2, \quad \text{II}$$

in which the remaining functional groups and also the functional groups $L^n$ (n=2–6 or 3–6, respectively) are optionally protected with a donor III $$L^8-A-(Y)_n-B-L^7 \quad \text{III}$$

which is provided with an activated functional group $L^7$ and, if $L^2$ is also unprotected, with a donor IV $$L^7-(D)_a-(Q)_r-E-L^8 \quad \text{IV,}$$

which is provided with an activated functional group $L^7$, whose remaining functional groups, and the functional group $L^8$, optionally carry protecting groups, intermediate compound V $$L^8-A-(Y)_n-B-CH-\underset{\underset{L^5}{|}}{\overset{\overset{L^3}{|}}{\underset{(K)_t}{\overset{(L)_p}{|}}}}-(C)_r-\underset{\underset{L^6}{|}}{\overset{\overset{L^4}{|}}{\underset{(L)_w}{\overset{(K)_q}{|}}}}-CH\underset{z}{\underbrace{-(D)_a-(Q)_v-E}}-L^8 \quad \text{V}$$

is initially prepared, where the donors III and IV can be different or identical, after which the functional groups of the intermediate compound V on the atom groups K and L and, optionally, the protecting groups of the functional groups $L^3$ to $L^6$ and $L^8$ are selectively removed and the selectively deprotected intermediate compound V is reacted with one or more glycosyl or polyol donors VI $$L^9-Z \quad \text{VI}$$

where $L^9$ is an activated functional group and the remaining functional groups of the donor VI are optionally protected, and, after selective deprotection of the functional groups $L^8$, alkylated with the alkyl donor VII $$\begin{array}{c} COOL^{10} \\ | \\ (CH_2)_l \\ | \\ R^5-V^1-L^{11} \\ | \\ (CH_2)_m \\ | \\ COOL^{10} \end{array} \quad \text{VII}$$

and, optionally with the alkyl donor VIII $$\begin{array}{c} COOL^{10} \\ | \\ (CH_2)_y \\ | \\ L^{11}-V^2-R^6 \\ | \\ (CH_2)_x \\ | \\ COOL^{10}, \end{array} \quad \text{VIII}$$

where $L^{10}$ is a carboxyl protecting group and $L^{11}$, optionally in combination with $V^1$ or $V^2$, is an alkylating group, and is finally converted, by removing all the protecting groups, into a compound of the formula I as claimed in claim 1.

21. The process as claimed in claim 20, wherein acceptor II is first reacted with one or more glycosyl or polyol donors of the formula VI and then with donor III and, optionally, with donor IV.

22. A pharmaceutical composition which comprises at least one compound of the formula I as claimed in claim 1, or its pharmacologically tolerated salts, and a pharmaceutically acceptable excipient or adjuvant.

23. A process for treating a disease which is associated with an excessive, selectin receptor-mediated cell adhesion, comprising administering the compound of the formula I, as claimed in claim 1, to a patient in need thereof.

24. The process of claim 23, wherein the disease is an autoimmune disease.

25. The process of claim 23, wherein the disease is a cardiovascular disease.

26. The compound of claim 1, wherein formula I is

[Chemical structure]

27. The compound of claim 1, wherein formula I is

[Chemical structure]

28. The compound of claim 1, wherein formula I is

[Chemical structure]

29. The compound of claim 1, wherein formula I is

[Chemical structure]

30. The compound of claim 1, wherein formula I is

[Chemical structure]

* * * * *